United States Patent [19]

Burks

[11] Patent Number: Plant 5,843

[45] Date of Patent: Dec. 30, 1986

[54] ROSE PLANT NAMED 'CITY OF ROSEMEAD'

[75] Inventor: Joe J. Burks, Tyler, Tex.

[73] Assignee: City of Rosemead, Rosemead, Calif.

[21] Appl. No.: 709,313

[22] Filed: Mar. 7, 1985

[51] Int. Cl.[4] ..... A01H 5/00

[52] U.S. Cl. ..... Plt./21

[58] Field of Search ..... Plt./21

*Primary Examiner*—James R. Feyrer

*Attorney, Agent, or Firm*—Vincent G. Gioia

[57] ABSTRACT

A new hybrid tea rose variety of Chrysanthemum crimson coloring which is a sport of the rose known as "Poinsetta".

2 Drawing Figures

The present invention relates to a new and distinct variety of rose plant of the hybrid tea rose class, which is a sport (mutation) of the rose known as "Poinsetta" which was discovered by me in Tyler, Tex. The denomination of this new rose is "City of Rosemead".

Among the novel characteristics possessed by this new variety which distinguish it from the cultivar from which it sported and all other varieties of which I am aware are its flowers which are much heavier petalled than its parent cultivar and much darker red in coloring. The foliage and plant habit of the new variety are very similar to that of the parent. The parent rose, known as "Poinsetta" is an old hybrid tea rose with large, double flowers, about 25 to 28 petals, and tending toward scarlet coloring. The new variety produces large flowers of 36 to 40 petals and the color tends toward Chrysanthemum crimson. The foliage of the new variety retains the same attractive dark green glossy appearance of its parent. Asexual reproduction by budding of the new variety as performed in Los Angeles County, Calif., shows that the foregoing and other distinguishing characteristics come true to form and are established and transmitted through succeeding propagations.

The accompanying drawings show typical specimens of flowers of the new variety in different stages of development and as depicted in color as nearly true as it is reasonably possible to make the same in a color illustration of this character.

The following is a detailed description of my new variety, with color terminology in accordance with The Royal Horticultural Society Colour Chart (R.H.S.C.C.). The terminology used in color description herein refers to plate numbers in the aforementioned color chart, e.g., "185A" is plate 185A of The Royal Horticultural Society Colour Chart.

Parentage: Sport (mutation) of the rose known as "Poinsetta".

Class: Hybrid Tea.

The following observations are made of specimens grown outdoors in Los Angeles County, Calif., during the month of November.

FLOWER

Blooming habit: Near continuous.

A. Bud:

(1) *Size.*—Medium to large.

(2) *Form.*—Long pointed.

(3) *Color.*—After sepals fall, bud color is a somewhat darker shade of Chrysanthemum crimson, 185A.

(4) *Sepals.*—Longer than bud, some foliated some simple.

(5) *Peduncle.*—Length — long. Aspect — strong. Strength — erect. Color — near 189A.

B. Bloom:

(1) *Size.*—Average size when fully expanded — about 4½ to 5 inches.

(2) *Borne.*—Singly; one to a stem.

(3) *Form.*—High centered at first becoming loose at maturity; outer petals quill, inner petals roll under.

(4) *Petalage.*—Number of petals under normal conditions — about 36 to 40.

(5) *Color.*—As petals unfurl from buds, Chrysanthemum crimson flower coloring, near 185A, remains fairly constant. Color of petal top and bottom surfaces is relatively similar but petal undersurface may appear lighter due to different texture and light reflectivity. Petal veining is also more visible on petal undersurface. Thus, depending upon light reflection, color of petal undersurface appears either substantially the same as petal top surface or somewhat lighter. Color at point of petal attachment is pale yellow. Outer petals occasionally show vertical white streaking. Despite heavy petalage, flowers open fully revealing petaloids and large array of stamens and stigma.

C. Petals:

(1) *Texture.*—Thick, very good substance.

(2) *Appearance.*—Top surface is velvety, undersurface is matte with veining.

(3) *Form.*—Wide oval.

(4) *Arrangement.*—Imbricated.

(5) *Petaloids in center.*—Some, large, misshapen.

(6) *Persistence.*—Persistent.

(7) *Fragrance.*—Slight.

(8) *Lasting quality.*—Long lasting on plant and as cut flower.

REPRODUCTIVE ORGANS

A. Stamens, filaments and anthers:

(1) *Arrangement.*—Many, irregular arrangement, outer row longer and incurved.

(2) *Color.*—Near 11D.

B. Pollen:

*Color.*—Yellow.

C. Styles: Uneven length, near 46A.

D. Stigmas:

*Color.*—Pale orange-yellow.

E. Hips: None observed.

PLANT

A. Form: Upright and slightly spreading.

B. Growth: Vigorous, uniform branching with large basals appearing in late summer.

*Height attained.*—About 4 to 4½ feet.

C. Foliage: Compound 5 leaflets.

(1) *Size.*—Medium.

(2) *Quantity.*—Ordinary.

(3) *Color.*—New foliage: light green. Old foliage: Upper side — near 133A. Under side — near 133C.

(4) *Shape.*—Oval, acuminate.

(5) *Texture.*—Upper side is glossy and under side is matte.

(6) *Edge.*—Serrated.

(7) *Serration.*—Simple.

(8) *Leaf stem.*—Color — near to 137A.

(9) *Stipules.*—Short.

(10) *Resistance to disease.*—Blackspot — average. Mildew — average. Rust — average.

D. Wood:

(1) *New wood.*—Color — near 137B. Bark — smooth.

(2) *Old wood.*—Color — near 137A. Bark — smooth.

E. Thorns:

(1) *Thorns.*—Quantity (main stalk) — ordinary. On laterals from stalk — ordinary. Form — slender, recurved. Length — medium. Color — tan.

(2) *Prickles.*—None.

F. Winter hardiness: Average.

I claim:

1. A new and distinct variety of rose plant of the hybrid tea class which is a sport of the rose known as "Poinsetta", substantially as shown and described, characterized particularly by heavily petalled flowers of Chrysanthemum crimson borne primarily one to a stem on a plant similar to its parent.

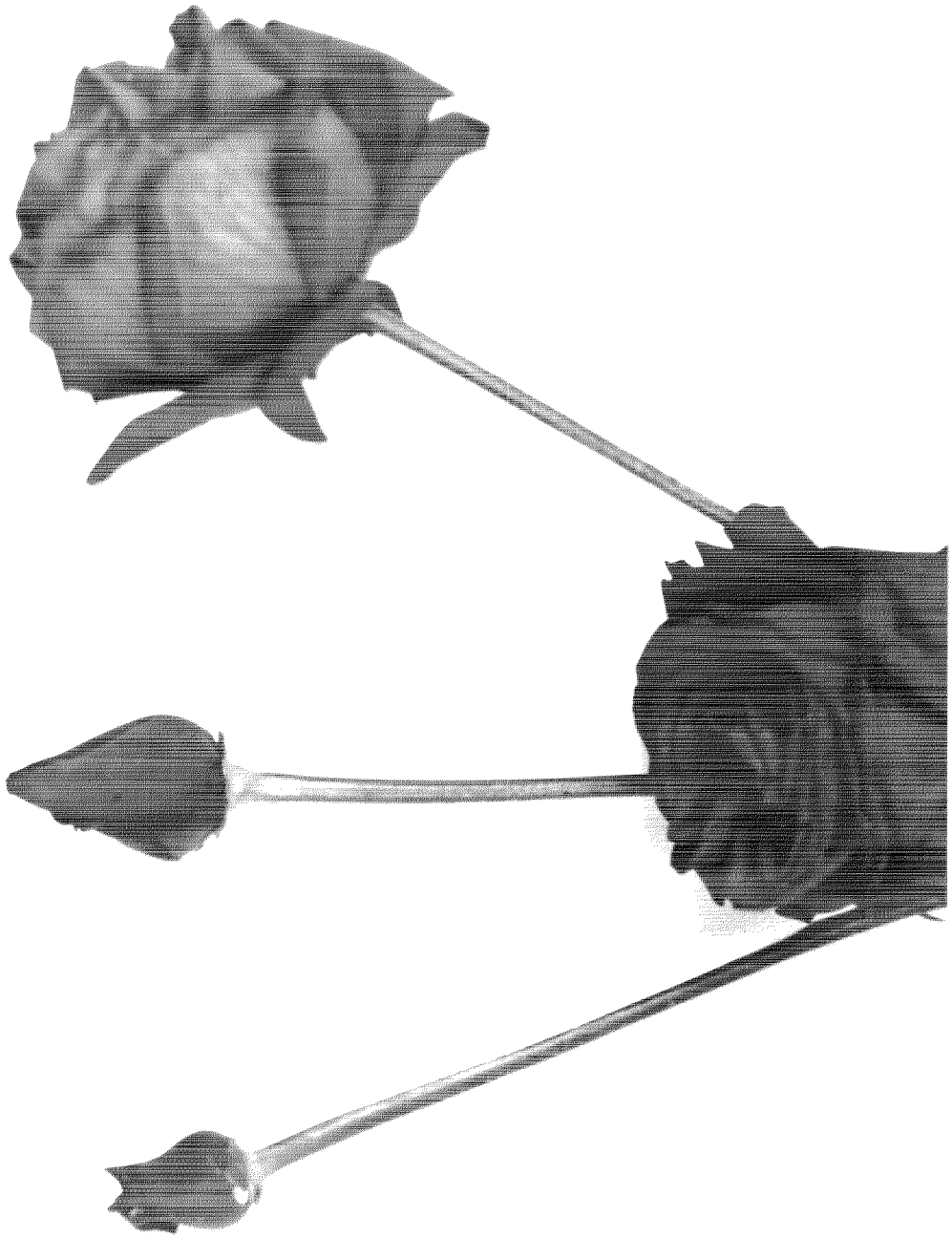

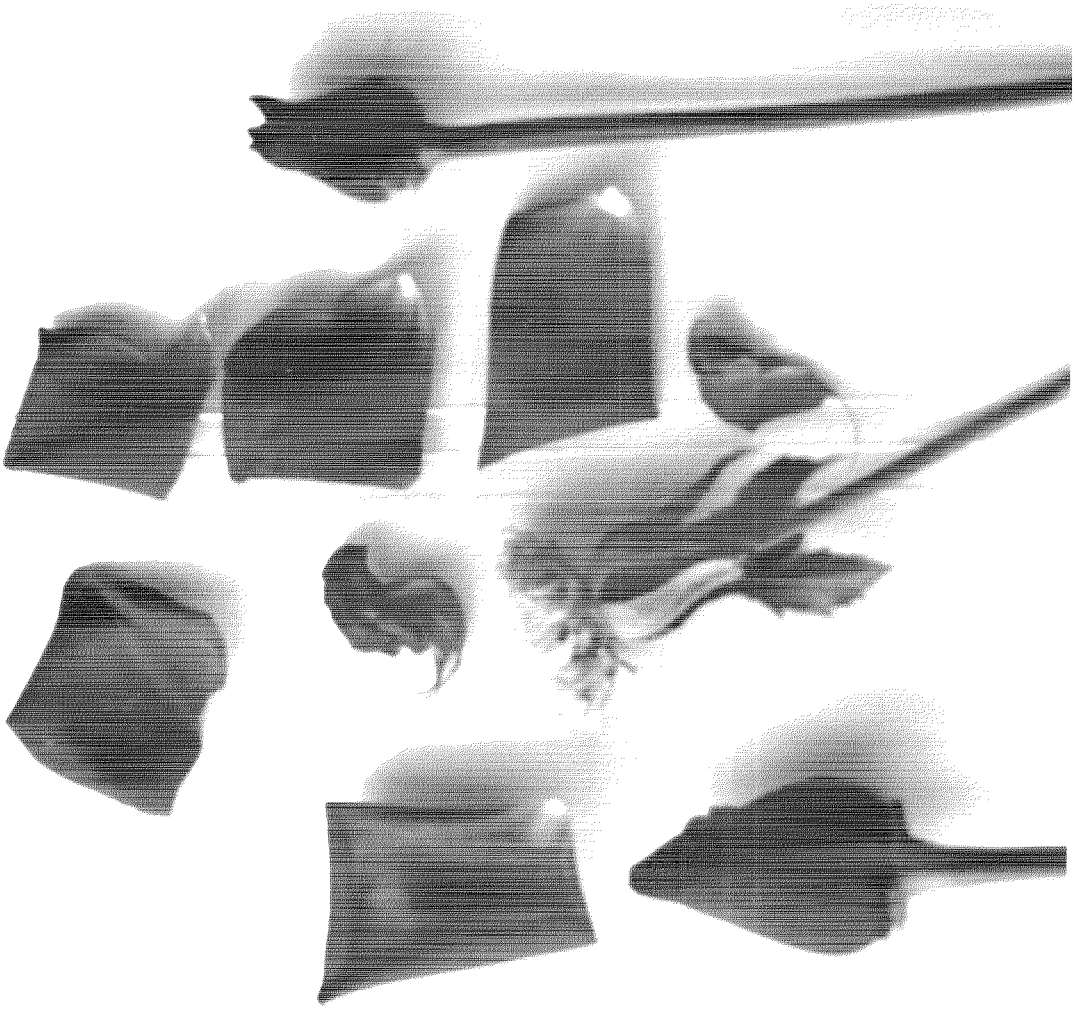

* * * * *